(12) United States Patent
Li et al.

(10) Patent No.: US 9,285,273 B2
(45) Date of Patent: Mar. 15, 2016

(54) OPTICAL FIBER-BASED ENVIRONMENTAL DETECTION SYSTEM AND THE METHOD THEREOF

(71) Applicant: Macau University of Science and Technology, Taipa (MO)

(72) Inventors: Jianqing Li, Taipa (MO); Ben Xu, Taipa (MO)

(73) Assignee: Macau University of Science and Technology, Macau (CN)

( * ) Notice: Subject to any disclaimer, the term of this patent is extended or adjusted under 35 U.S.C. 154(b) by 323 days.

(21) Appl. No.: 14/146,727

(22) Filed: Jan. 3, 2014

(65) Prior Publication Data

US 2015/0168216 A1 Jun. 18, 2015

Related U.S. Application Data

(60) Provisional application No. 61/916,803, filed on Dec. 17, 2013.

(51) Int. Cl.
| | |
|---|---|
| *G01K 11/00* | (2006.01) |
| *G01J 3/45* | (2006.01) |
| *G01J 3/02* | (2006.01) |
| *G01J 3/10* | (2006.01) |
| *G01K 11/32* | (2006.01) |

(52) U.S. Cl.
CPC .................. *G01J 3/45* (2013.01); *G01J 3/0218* (2013.01); *G01J 3/10* (2013.01); *G01K 11/3206* (2013.01)

(58) Field of Classification Search
CPC .............. G01K 11/65; G01J 3/45; G01J 5/08; G01B 9/02

USPC ........... 374/162, 161, 130, 131; 356/477, 450
See application file for complete search history.

(56) References Cited

U.S. PATENT DOCUMENTS

| 7,602,499 B2 * | 10/2009 | Lecoeuche | G01M 11/336 356/491 |
| 8,125,648 B2 * | 2/2012 | Milner | A61B 1/00096 356/497 |
| 2011/0277552 A1 * | 11/2011 | Chen | G01M 11/331 73/763 |
| 2013/0321818 A1 * | 12/2013 | Yao | G01J 4/02 356/477 |

* cited by examiner

*Primary Examiner* — Lisa Caputo
*Assistant Examiner* — Nigel Plumb
(74) *Attorney, Agent, or Firm* — Eagle IP Limited; Jacqueline C. Lui

(57) ABSTRACT

An optical fiber environmental detection system comprising an interferometer, a broadband light source and a detector is disclosed. The interferometer further comprises a thin core fiber, a first single mode fiber and a second single mode fiber; wherein the thin core fiber is coupled to the first and second single mode fiber via a first junction and a second junction respectively. When an emission light reaches the first junction, high-order cladding modes will be excited. The excited cladding modes will interfere with the core mode at the second junction. The interferences determine the intensity maximum or minimum of the received signal. When there is an ambient environmental change, a shift of the received signal would be induced. According to the shift, environmental change, for instance ambient temperature, could be determined.

20 Claims, 9 Drawing Sheets

OPTICAL FIBER-BASED ENVIRONMENTAL DETECTION SYSTEM AND THE METHOD THEREOF

CROSS-REFERENCE TO RELATED APPLICATION

This application claims benefit under 35 U.S.C. §119(e) of U.S. Provisional application having Ser. No. 61/916,803 filed 17 Dec. 2013, which is hereby incorporated by reference herein in its entirety.

FIELD OF INVENTION

This invention relates to an environmental detection system and in particular an optical fiber-based environmental detection system.

BACKGROUND OF INVENTION

Traditional optical fiber-based environmental detection system, for instance temperature measurement, can be achieved by using various optical fiber devices. Commonly used optical fiber devices include fiber Bragg gratings (FBGs), long-period fiber gratings (LPFGs) and fiber interferometers. Among them, FBGs are widely known for their small size and wavelength multiplexing capability, but the temperature sensitivity is relatively low (around 10 pm/° C.). LPFGs can have much higher sensitivity, but they suffer from cross-sensitivity to surrounding refractive index (SRI) and fiber bending. Optical fiber interferometers based on any of the cavity structures are highly sensitive, simple and relatively inexpensive. Some interferometric temperature sensors with sensitivity of about 12.9-118.6 pm/° C. have been demonstrated by splicing a section of multimode fiber (MMF) or thin-core fiber (TCF), or hollow core fiber (HCF) between two single-mode fibers (SMFs). Recently, to fill liquid with high thermo-optic coefficient into photonic crystal fiber (PCF) interferometers can achieve a highly sensitivity of nm/° C. order of magnitude. However, to fill liquid into the specific micro air holes of the PCF is quite complicated and a large SRI cross-sensitivity still exists.

SUMMARY OF INVENTION

In the light of the foregoing background, it is an object of the present invention to provide an alternate design of high sensitive environmental detection system. The proposed environmental detection system is simple, easy to fabricate and intrinsically is avoidable to cross-sensitivity problem.

Accordingly, the present invention, in one aspect, is an environmental detection system comprising: (a) an interferometer which comprises a thin core fiber, a first single mode fiber and a second single mode fiber; wherein the thin core fiber has a core diameter thinner than that of the first and the second single mode fiber and is coupled to the first single mode fiber via a first junction and to the second single mode fiber via a second junction; (b) a broadband light source configured to emit an emission light and coupled to the first single mode fiber of the interferometer; thereby allowing the emission light to propagate from the first single mode fiber to the second single mode fiber through the thin core fiber; and (c) a detector coupled to the second single mode fiber of the interferometer and configured to capture a signal from the interferometer. The first junction creates a plurality of optical paths for the emission light to transmit through the interferometer and the second junction collects those optical paths to the second single mode fiber. When there is an environmental change, the optical paths will be altered and thus inducing a shift of the signal which is detected by the environmental detection system.

In one embodiment, when the emission light reaches the first junction, high-order cladding modes will be excited. The excited high-order cladding modes will interfere with the core mode at the second junction due to the existing optical path difference between the two modes. The constructive or destructive interference will determine the maximum or minimum (corresponding to the peak or dip in a spectrum) of the received signal. When there is an environmental temperature change, the peak or dip will shift to shorter or longer wavelength. And the environmental change could be determiner according to the shift.

In an exemplary embodiment of the present invention, the interferometer further comprises a capillary tube filled with a refractive index liquid; wherein the thin core fiber, the first single mode fiber and then second single mode fiber are encapsulated within the capillary tube.

In another exemplary embodiment, the detector is an optical spectrum analyzer and the signal is in a form of optical spectrum; wherein the optical spectrum analyzer further comprises a microprocessor and a computer-readable storage media; wherein the computer-readable storage media is coupled to the microprocessor and is encoded with non-transitory computer-readable instructions for causing the microprocessor to execute the steps of determining the shift of the optical spectrum; and obtaining a value of the environmental change based on the shift.

According to another aspect of the present invention, a method of detecting an environmental change is provided. The method comprises the steps of: (a) providing an interferometer comprising a thin core fiber, a first single mode fiber and a second single mode fiber; wherein the thin core fiber has a core diameter thinner than that of the first single mode fiber and the second mode fiber and is coupled to the first single mode fiber via a first junction and to the second single mode fiber via a second junction; (b) directing a broadband light beam to the first single mode fiber of the interferometer; (c) passing the broadband light beam to the thin core fiber via the first junction, thereby creating a plurality of optical paths at the first junction; (d) collecting the plurality of optical paths at the second junction, thereby obtaining a signal at the second single mode fiber; and (e) determining the environmental change based on a shift of the signal; wherein the environmental change alters the optical paths thereby inducing the shift of the signal.

In an exemplary embodiment, the step of providing the interferometer further comprises the steps of: (a) removing the coating of the thin core fiber; (b) splicing the thin core fiber between the first single mode fiber and the second single mode fiber of the interferometer and (c) etching a middle section of the thin core fiber using an acidic solution; thereby forming a biconical tapered fiber.

In one embodiment, the method further comprises the steps of: encapsulating the interferometer into a capillary tube; and filling the capillary tube with a refractive index liquid, wherein the refractive index of the refractive index liquid changes according to the environmental change.

In another embodiment, the signal is in a form of optical spectrum and the step of determining the environmental change further comprises the steps of: determining a wavelength shift of the optical spectrum; and obtaining a value of the environmental change based on the wavelength shift.

There are many advantages to the present invention. In particular, the present invention provides a highly sensitive temperature sensor with simple structure. Such design reduces both the complexity and the cost of the system. Another advantage of the present invention is that the sensor does not suffer from cross-sensitivity to surrounding refractive index (SRI) and fiber bending.

BRIEF DESCRIPTION OF FIGURES

FIG. 5b shows the analyzed result of the transmission spectra as shown in FIG. 5a.

FIG. 6b shows the analyzed result of the transmission spectra as shown in FIG. 6a.

DETAILED DESCRIPTION OF THE PREFERRED EMBODIMENTS

As used herein and in the claims, "comprising" means including the following elements but not excluding others.

Figure 1:
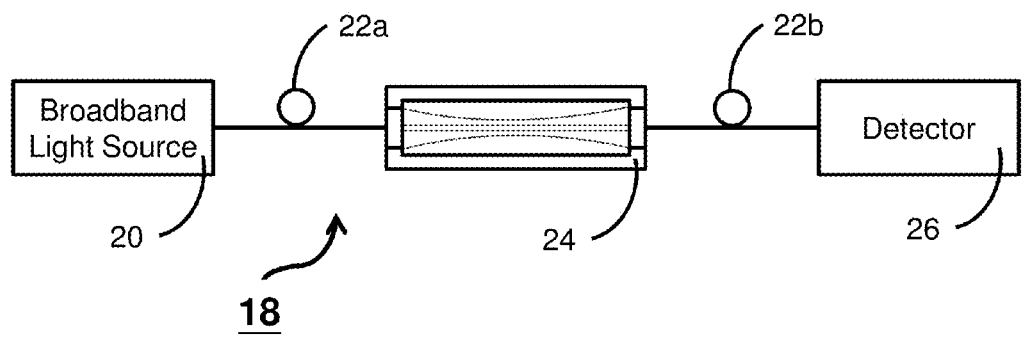
FIG. 1 is a schematic diagram of the environmental detection system according to one of the embodiments of the present invention.

Referring now to FIG. 1, the first aspect of the present invention is an environmental detection system 18. The environmental detection system 18 comprises a broadband light source 20, an interferometer 24 and a detector 26. The broadband light source 20 is coupled to a first end of the interferometer 24 via a single mode fiber 22a. On the other hand, the detector 26 is couple to a second end, which is longitudinal opposite to the first end, of the interferometer 24 via another single mode fiber 22b.

Figure 2:
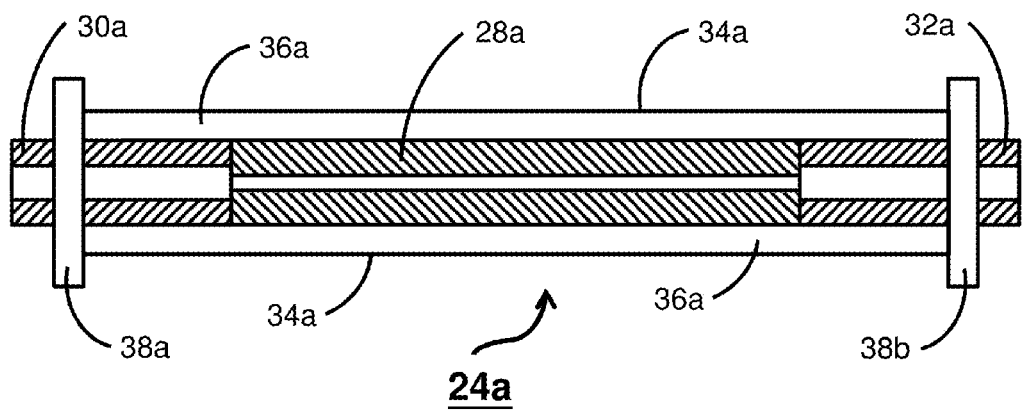
FIG. 2 is a longitudinal sectional view of the interferometer according to one of the embodiments of the present invention.

Referring now to FIG. 2, the interferometer 24a according to one embodiment of the present invention is shown. The interferometer 24a comprises a thin core fiber 28a, a first single mode fiber 30a and a second single mode fiber 32a; wherein the thin core fiber 28a is sandwiched therebetween thereby forming a first junction and a second junction. The thin core fiber 28a, the first single mode fiber 30a and the second single mode fiber 32a are then sealed in a capillary tube 34a, which is filled with a refractive index liquid 36a, using glues 38a and 38b. The capillary tube 34a prevents any bending of the thin core fiber 28a, the first single mode fiber 30a and the second single mode fiber 32a, which is essential to maintain the repeatability and stability of the environmental detection system 18. The emission light emitted by the broadband light source 20 (as shown in FIG. 1) is directed to the interferometer 24a via the first single mode fiber 30a. When the emission light reaches the first junction (i.e. the hetero-core interface between the first single mode fiber 30a and the thin core fiber 28a), high-order cladding modes will be excited. The excited high-order cladding modes will interfere with the core mode at the second junction (i.e. the hetero-core interface between the thin core fiber 28a and the second single mode fiber 32a). The interference (constructive or destructive) will determine the wavelength of the signal received by the detector 26 (as shown in FIG. 1). When there is a change of the ambient environment, the refractive index of the refractive index liquid 36a will change and the interference fringe of the shift accordingly. As a result, the environmental change can be determined by analyzing the received signal and determining the shift.

Figure 3:
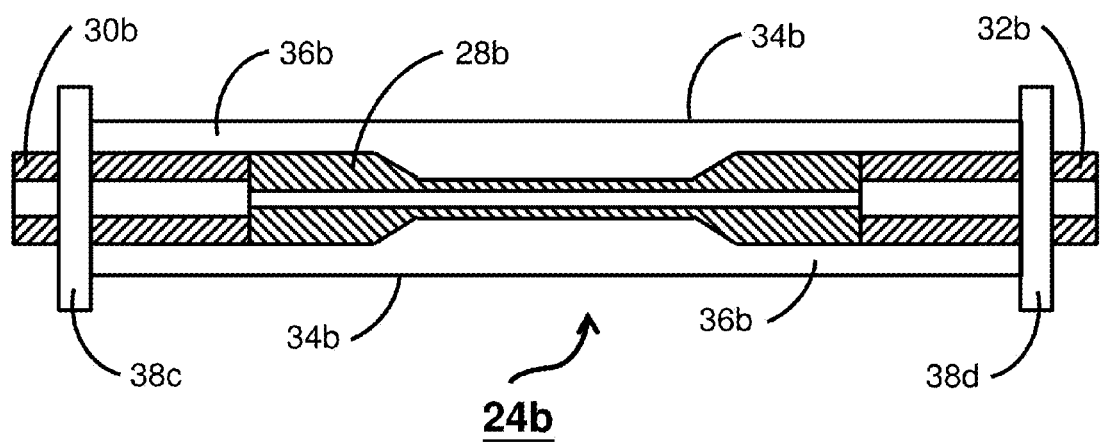
FIG. 3 is a longitudinal sectional view of the interferometer according to another embodiment of the present invention.

According to another embodiment of the present invention, as shown in FIG. 3, the thin core fiber of the interferometer 24b is a biconical taper 28b. The biconical taper 28b is formed by removing the coating of a thin core fiber and etching the middle section of the thin core fiber using an acidic solution. In one embodiment, the acidic solution used is hydrofluoric acid. In a specific embodiment, the length and diameter of said biconical taper waist is in the range of 2 mm to 30 mm and 10 μm to 50 μm respectively. The biconical taper 28b, the first single mode fiber 30b and the second single mode fiber 32b are sealed in a capillary tube 34b which is filled with refractive index liquid 36b, with glue 38c and 38d. In the taper waist region of the biconical taper 28b, due to the thinner cladding diameter, the interaction between high order cladding modes and the refractive index liquid 36b become stronger. As a result, the interferometer 24b is more sensitive to surrounding refractive index resulting in a higher sensitivity to environmental change.

In one embodiment, the refractive index liquid 36a or 36b is a liquid selected from a group consist of Cargille oil, ethanol, isopropanol; which has a thermo-optic coefficient of −3.0 to −4.5*10$^{-4}$/° C. In another embodiment, the capillary tube 34a or 34b is made of material selected from a group consisting of quartz, silicate glass and steel; and the inner diameter of the capillary tube 34a or 34b is in the range of 150 μm-2000 μm. In a further embodiment, the diameter and the core diameter of the thin core fiber 28a is 125 μm and 2-5 μm respectively. In one embodiment, the glues 38a, 38b, 38c and 38d are AB glues.

In one embodiment, the broadband light source 20 and detector 26 as shown in FIG. 1 are a super luminescent light emitting diode and optical spectrum analyzer respectively. The corresponding signal as captured by the detector 26 is in a form of optical spectrum. In a specific embodiment, the detector 26 further comprises a microprocessor (not shown) and computer-readable storage media (not shown). The computer-readable storage media is coupled to the microprocessor and is encoded with non-transitory computer-readable instructions for causing the microprocessor to execute the following steps: determining a shift of the optical spectrum; and obtaining a value of the environmental change based on the shift. In one embodiment, the shift refers to the dip wavelength shift of the optical spectrum.

Figure 4:
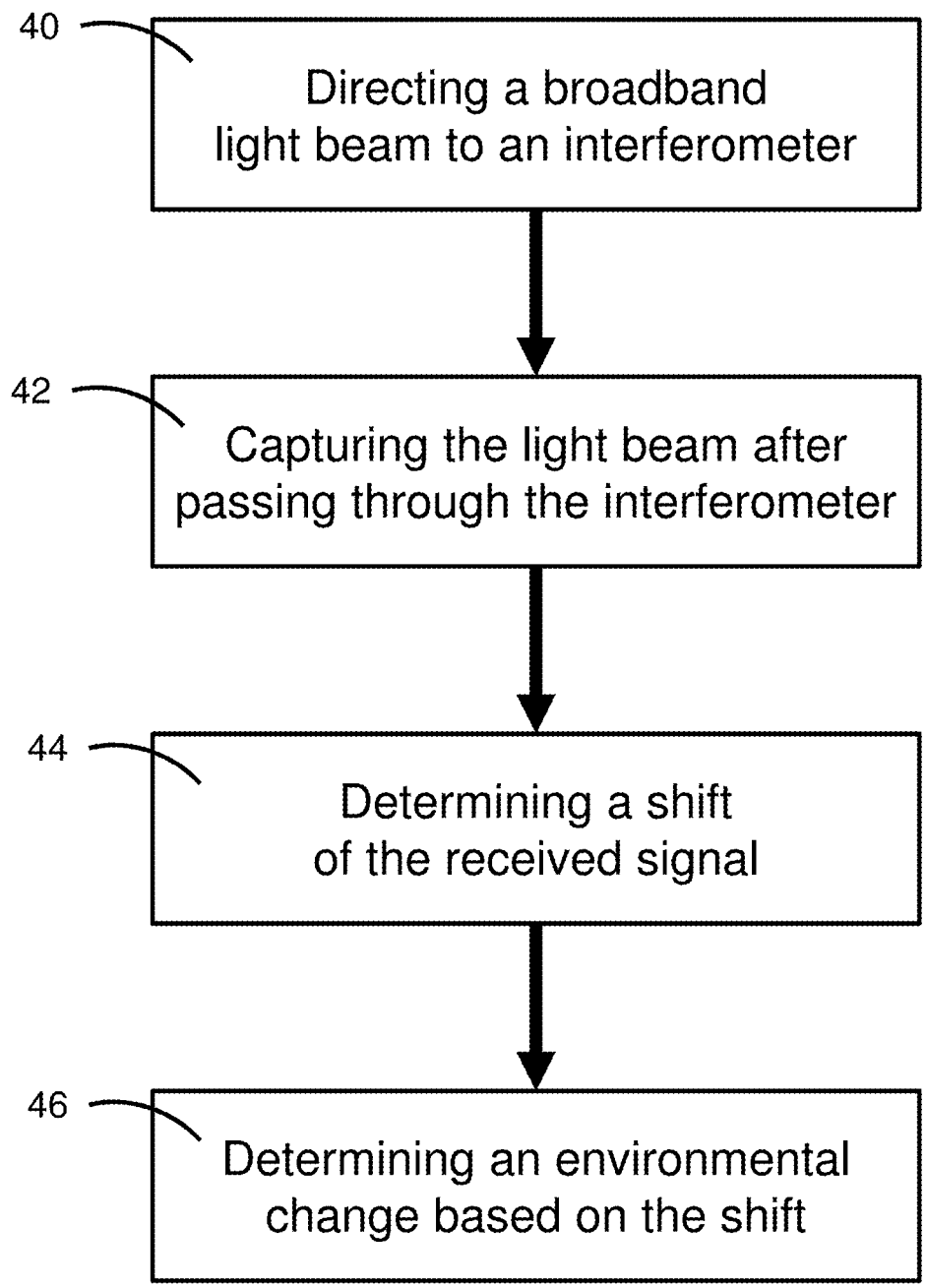
FIG. 4 is a flow chart of the method of detecting an environmental change according to an embodiment of the present invention.

According to another aspect of the present invention, a method of detecting temperature is provided. Referring to FIG. 4, the first step 40 of the method is to direct a broadband light beam to the interferometer. In the second step 42 of the present invention, the light beam, after passing through the interferometer, is captured. Afterwards, the received signal is analyzed and the shift of the determined in step 44. Finally, the environmental change is determined based on the shift in step 46.

In one embodiment, the method further comprises a step of providing an interferometer as described above. The broadband light beam is directed to the first single mode fiber of the interferometer; whereas the received signal is received at the second single mode fiber of the interferometer. In another embodiment, the step of providing the interferometer further comprises the steps of: (a) removing coating of the thin core fiber; (b) splicing the thin core fiber between the first single mode fiber and the second single mode fiber and (c) etching a middle section of the thin core fiber using an acidic solution; thereby forming a biconical tapered fiber. In one embodiment, the acidic solution used is hydrofluoric acid.

In a specific implementation of the present invention, the environmental change of interest is temperature change and the method of detecting the environmental change further comprises the steps of: (a) predefining a temperature response function of the interferometer; and (b) obtaining a temperature value by inputting the shift of the received signal to the temperature response function. The temperature response is obtained by first obtaining a plurality of received signal, for instance optical spectra. Each of the optical spectra is obtained under a different predefined ambient temperature. After a predefined number of optical spectra are obtained, the shift of each optical spectrum is determined. In one specific implementation, the temperature response function refers to the relationship between the shifts and the predefined ambient temperatures, which can be obtained by using polynomial fitting.

Figure 5A:
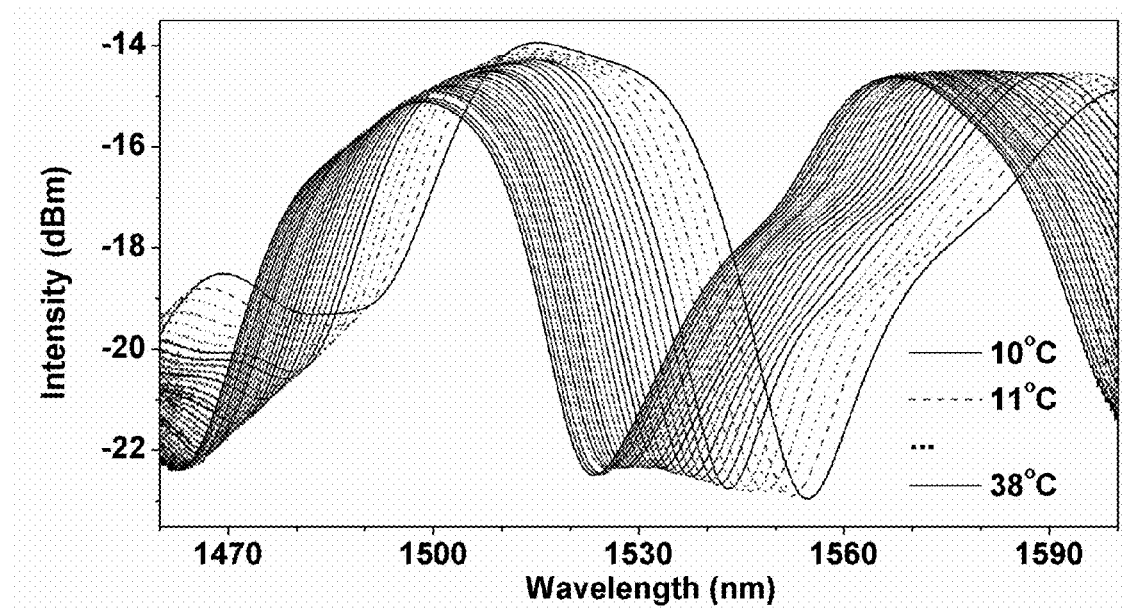
FIG. 5a shows the transmission spectra of the interferometer according to the embodiment of the present invention shown in FIG. 2.
Figure 5B:
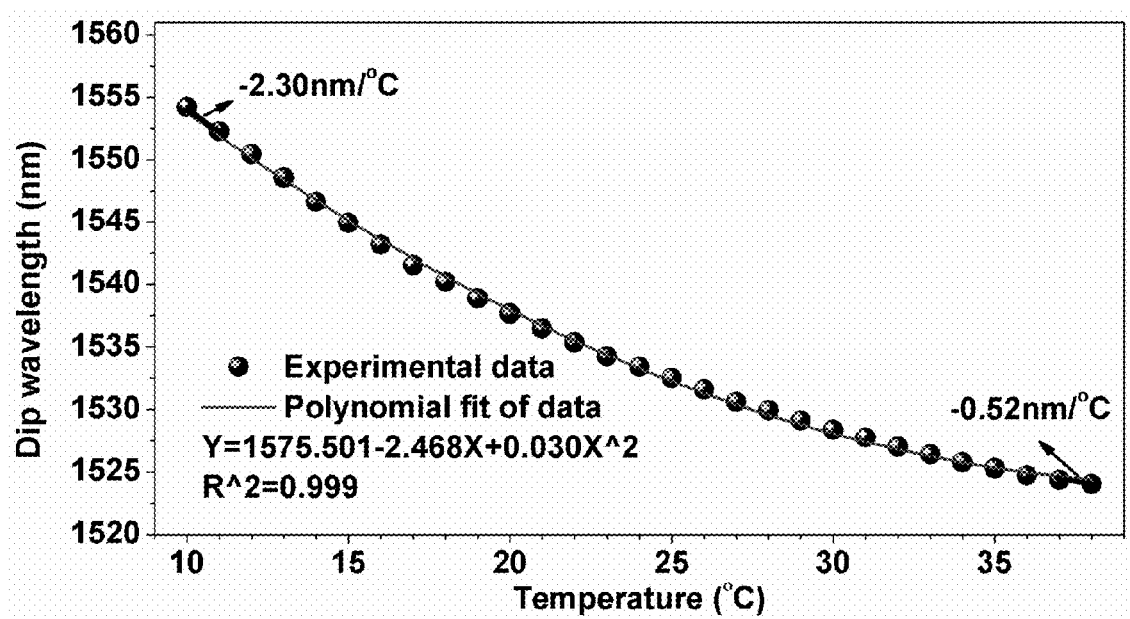
Figure 5C:
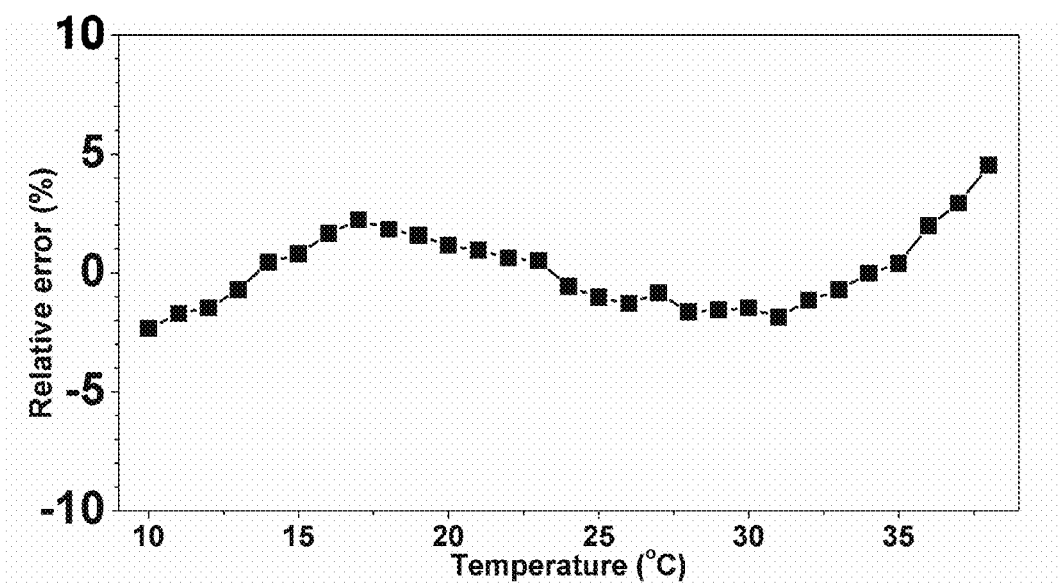
FIG. 5c shows the fitting error of the analyzed result as shown in FIG. 5b.

In order to verify the feasibility of the environmental detection system proposed in the present invention, a temperature sensor, as an illustrative example, with structure as shown in FIG. 2 was fabricated. The length of thin core fiber is 20 mm and the interferometer is sealed in a capillary tube made of silicate glass and filled with Cargiller oil (from Cargille Labs) which has a nominal RI value of 1.44. A super luminescent light emitting diode is used as the broadband light source and an optical spectrum analyzer is used as the detector to receive and to analyze the received optical spectrum. The measured transmission spectra versus temperatures are shown in FIG. 5a. Tracing the resonance dip with a large extinction-ratio at near 1550 nm, it is found that the resonance dip shifts greatly to shorter wavelength with the increasing of temperature. FIG. 5b displays the measured dip wavelengths at different temperatures. A second-order polynomial is used to fit the dip wavelengths across the entire calibration range, and the Adj. R-Square is 0.999. FIG. 5c shows the fitting error on temperature, it can be seen, within the tested temperature range, the fitting error is smaller than 5%. It is found that the temperature sensor is very sensitive to the ambient temperature, and it is feasible to apply this sensor for temperature sensing.

Figure 6A:
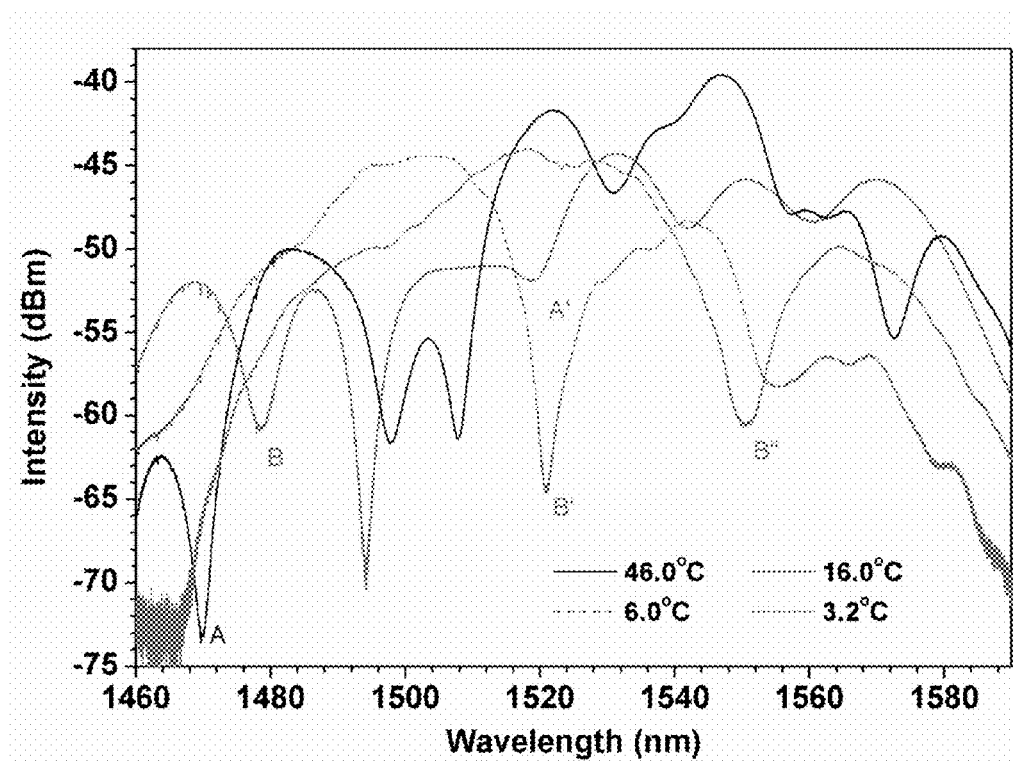
FIG. 6a shows the transmission spectra of the interferometer according to the embodiment shown in FIG. 3.
Figure 6B:
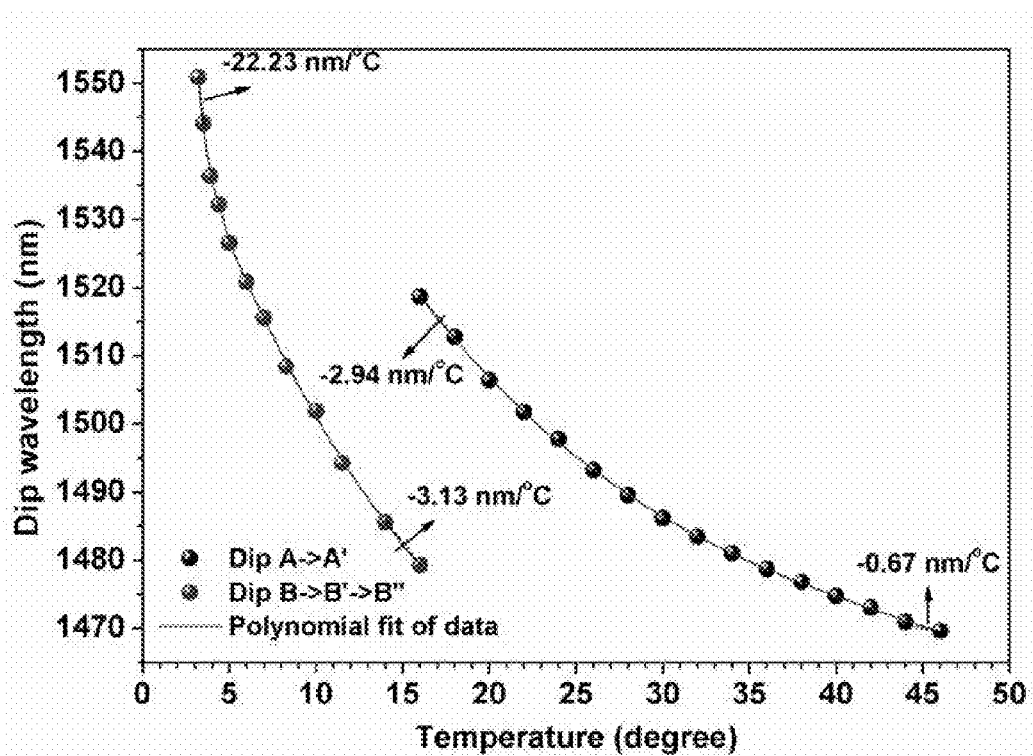
Figure 6C:
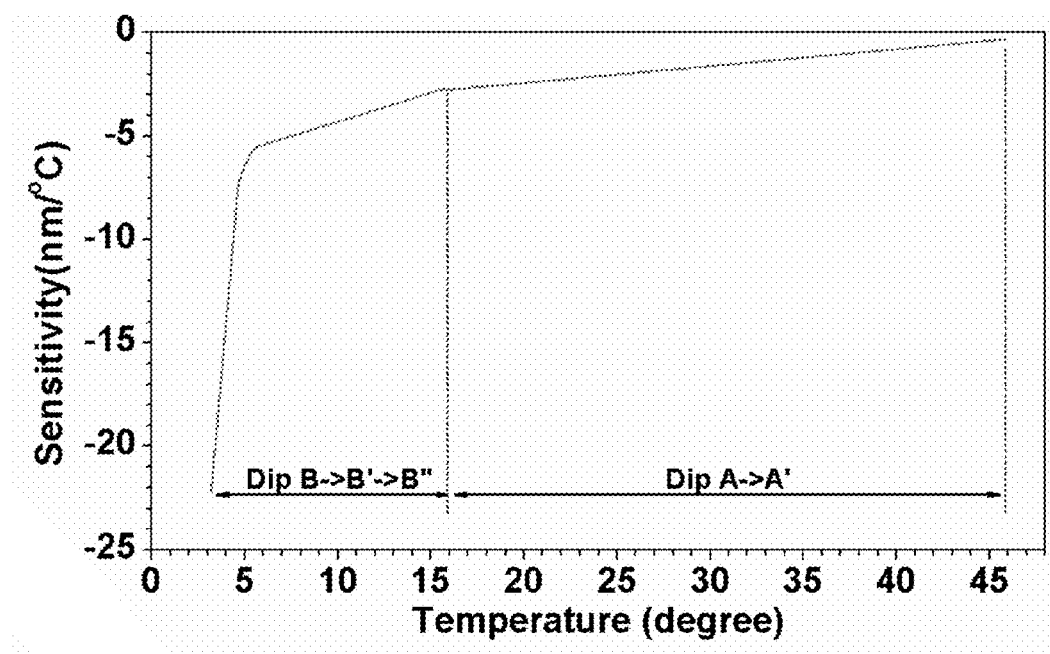
FIG. 6c shows the sensitivity versus temperature of the environmental detection system according to the same embodiment as shown in FIG. 6a and FIG. 6b.

Another temperature sensor as described in FIG. 3 was also fabricated and tested so as to demonstrate the sensitivity improvement when a biconical thin core taper is used in the interferometer. The total length of the thin core fiber is 30 mm, and the middle session of the thin core fiber was etched by hydrofluoric acid. The length and residue diameter of the taper waist is about 20 mm and 20 µm, respectively. The cladding-etched interferometer was sealed in a capillary tube made of silicate glass and filled with Cargille oil (from Cargille Labs) which has a nominal RI value of 1.44. FIG. 6a shows the typical transmission spectra of this sensor under different ambient temperatures. It was found that, as the temperature changed from 46.0° C. to 16.0° C., the transmission dip A shifted over 50 nm to A' with a gradually reduced extinction ratio. A new transmission dip B was used to measure temperature in the range from 16.0° C. to 3.2° C., and it shifted over 70 nm to B" via B' achieved at 8.0° C. FIG. 6b shows the wavelengths against temperatures of the two tracing transmission dips (dip A and dip B as described in FIG. 6a). It indicates that the sensor produces a nonlinear response to temperature variations characterized by an ultrahigh sensitivity of −22.23 nm/° C. at the lowest tested temperature of 3.2° C. Referring to FIG. 6c, it indicates that the sensor with biconical thin core taper produces a nonlinear response to temperature variations characterized by an ultrahigh sensitivity.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, temperature sensors are provided as illustrative example of the present invention. It should be clear to one skilled in the art that the present invention is not limited to measurement of temperature; but can be used to measure any environmental parameters which could affect the refractive index of the refractive index liquid, for instance density.

Moreover, while wavelength dips are used in the aforementioned implementations as anchor points to track the changes of ambient temperature, other signal patterns in the graphs shown in FIGS. 5a and 6a can also be used. For example, the peak responses, or a combination of valleys and peaks may also be used. Those skilled in the art, based on the teaching of this invention, may also apply digital signal processing techniques to analyze the detected signal and identify salient patterns, whether in time-domain or frequency domain, as reference points for tracking environmental changes. Hence using the dips of the wavelength as anchor point is one of the many ways to realize this invention and it should not be construed that this is the only way to realize this invention.

What is claimed is:

1. An environmental detection system comprising:
a) an interferometer comprising a thin core fiber, a first single mode fiber and a second single mode fiber; wherein said thin core fiber has a core diameter thinner than said first single mode fiber and said second mode fiber and is coupled to said first single mode fiber via a first junction and to said second single mode fiber via a second junction;
b) a broadband light source configured to emit an emission light and coupled to said first single mode fiber of said interferometer; thereby allowing said emission light to propagate from said first single mode fiber to said second single mode fiber through said thin core fiber; and
c) a detector coupled to said second single mode fiber of said interferometer and configured to capture a signal from said interferometer;
wherein said first junction creates a plurality of optical paths for said emission light and said second junction collects said plurality of optical paths to said second single mode fiber such that an environmental change altering said optical paths, and inducing a shift of said signal is detected by said environmental detection system.

2. The environmental detection system of claim 1, wherein said interferometer further comprises a capillary tube filled with a refractive index liquid; wherein said thin core fiber, said first single mode fiber and said second single mode fiber are encapsulated within said capillary tube.

3. The environmental detection system of claim 2, wherein said refractive index liquid is a liquid selected from a group consisting of Cargille oil, ethanol and isopropanol; and said refractive index liquid has a thermo-optic coefficient of −3.0 to −4.5*$10^{-4}$/° C.

4. The environmental detection system of claim 2, wherein said capillary tube is made of material selected from a group consisting of quartz, silicate glass and steel; and the inner diameter of said capillary tube is in the range of 150 µm to 2000 µm.

5. The environmental detection system of claim 1, wherein the diameter of said thin core fiber is 125 μm and said core diameter of said thin core fiber is in the range of 2 μm to 5 μm.

6. The environmental detection system of claim 1, wherein said thin core fiber is a biconical taper; wherein the waist length and waist diameter of said biconical taper is in the range of 2 mm to 30 mm and 10 μm to 50 μm respectively.

7. The environmental detection system of claim 1, wherein said broadband light source is a super luminescent light emitting diode or amplified spontaneous emission light source.

8. The environmental detection system of claim 1, wherein said detector is an optical spectrum analyzer and said signal is in a form of optical spectrum; wherein said optical spectrum analyzer further comprises a microprocessor and a computer-readable storage media; wherein said computer-readable storage media is coupled to said microprocessor and is encoded with non-transitory computer-readable instructions for causing said microprocessor to execute the following steps:
   a) determining said shift of said optical spectrum; and
   b) obtaining a value of said environmental change based on said shift.

9. The environmental detection system of claim 8; wherein said environmental change is a temperature change and said shift is a dip wavelength shift of said optical spectrum.

10. A method of detecting an environmental change, wherein said method comprises the steps of:
   a) providing an interferometer comprising a thin core fiber, a first single mode fiber and a second single mode fiber; wherein said thin core fiber has a core diameter thinner than said first single mode fiber and said second mode fiber and is coupled to said first single mode fiber via a first junction and to said second single mode fiber via a second junction;
   b) directing a broadband light beam to said first single mode fiber of said interferometer;
   c) passing said broadband light beam to said thin core fiber via said first junction, thereby creating a plurality of optical paths from said at said first junction;
   d) collecting said plurality of optical paths at said second junction, thereby obtaining a signal at said second single mode fiber; and
   e) determining said environmental change based on a shift of said signal;
   wherein said environmental change alters said optical paths thereby inducing said shift of said signal.

11. The method of claim 10, wherein said step of providing said interferometer further comprises the steps of:
   a) removing coating of said thin core fiber;
   b) splicing said thin core fiber between said first single mode fiber and said second single mode fiber; and
   c) etching a middle section of said thin core fiber using an acidic solution; thereby forming a biconical tapered fiber.

12. The method of claim 10 further comprising the steps of:
   a) encapsulating said interferometer into a capillary tube; and
   b) filling said capillary tube with a refractive index liquid; wherein refractive index of said refractive index liquid changes according to said environmental change.

13. The method of claim 12, wherein said refractive index liquid is a liquid selected from a group consisting of Cargille oil, ethanol and isopropanol and said refractive index liquid has a thermo-optic coefficient of $-3.0$ to $-4.5*10^{-4}/°$ C.

14. The method of claim 12, wherein said capillary tube is made of material selected from a group consisting of quartz, silicate glass and steel; and the inner diameter of said capillary tube is in the range of 150 μm-2000 μm.

15. The method of claim 10 further comprising a step of submerging said interferometer into a refractive index liquid; wherein said refractive index liquid is a liquid selected from a group consisting of Cargille oil, ethanol and isopropanol; and said refractive index liquid has a thermo-optic coefficient of $-3.0$ to $-4.5*10^{-4}/°$ C.

16. The method of claim 10, wherein said broadband light beam is provided by coupling a super luminescent light emitting diode or amplified spontaneous emission (ASE) light source to said first single mode fiber of said interferometer.

17. The method of claim 10, wherein said signal is in a form of optical spectrum and said step of determining said environmental change further comprises the steps of:
   a) determining a shift of said optical spectrum; and
   b) obtaining a value of said environmental change based on said shift.

18. The method of claim 17; wherein said environmental change is a temperature change and said shift is a dip wavelength shift of said optical spectrum.

19. The method of claim 18 further comprising the steps of:
   a) predefining a temperature response function of said interferometer; and
   b) obtaining a temperature value by inputting said shift to said temperature response function.

20. The method of claim 19, wherein said step of predefining said temperature response function further comprising the iterative steps of:
   a) obtaining a plurality of optical spectra; wherein each of said plurality of optical spectra is obtained under a different predefined ambient temperature; and
   b) determining a plurality of wavelength shifts based on said plurality of optical spectra;
   wherein said iterative steps terminate when a predefined number of optical spectra is obtained; and said step of predefining said temperature response function further comprises a step of establishing a relationship between said plurality of wavelength shifts and said predefined ambient temperature; thereby generating said temperature response function.

* * * * *